(12) United States Patent
Reddy et al.

(10) Patent No.: US 7,056,953 B2
(45) Date of Patent: *Jun. 6, 2006

(54) (E)-STYRYL SULFONE ANTICANCER AGENTS

(75) Inventors: E. Premkumar Reddy, Villanova, PA (US); M. V. Ramana Reddy, Upper Darby, PA (US)

(73) Assignee: Temple University - of The Commonwealth System of Higher Education, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/848,454

(22) Filed: May 18, 2004

(65) Prior Publication Data

US 2004/0229959 A1 Nov. 18, 2004

Related U.S. Application Data

(63) Continuation of application No. 09/937,684, filed as application No. PCT/US00/08656 on Mar. 31, 2000, now Pat. No. 6,762,207.

(60) Provisional application No. 60/127,683, filed on Apr. 2, 1999, provisional application No. 60/143,975, filed on Jul. 15, 1999.

(51) Int. Cl.
*A01N 41/10* (2006.01)

(52) U.S. Cl. ..................................... 514/710
(58) Field of Classification Search ............... 514/710
See application file for complete search history.

(56) References Cited

U.S. PATENT DOCUMENTS

| | | | | |
|---|---|---|---|---|
| 2,532,612 A | 12/1950 | Doumani | .................... | 260/609 |
| 3,185,743 A | 5/1965 | Combe et al. | .............. | 260/682 |
| 3,418,101 A | 12/1968 | Buchholtz et al. | ............. | 71/72 |
| 3,463,774 A | 8/1969 | Wilhelm et al. | ......... | 260/239.3 |
| 3,514,386 A | 5/1970 | Oswald et al. | .............. | 204/162 |
| 3,917,714 A | 11/1975 | Richmond | .............. | 260/607 A |
| 4,161,407 A | 7/1979 | Campbell | .................... | 96/114 |
| 4,386,221 A | 5/1983 | Hyatt et al. | .................... | 568/28 |
| 4,937,388 A | 6/1990 | Bushell et al. | ................ | 568/56 |
| 5,659,087 A | 8/1997 | Aikins et al. | ................ | 568/27 |
| 5,733,909 A | 3/1998 | Black et al. | ............ | 514/238.8 |
| 6,201,154 B1 | 3/2001 | Reddy et al. | ................. | 508/28 |
| 6,359,013 B1 | 3/2002 | Reddy et al. | ............... | 514/710 |

FOREIGN PATENT DOCUMENTS

EP  WO 99/18068 * 4/1999

OTHER PUBLICATIONS

Kamigata et al., *Phosphorous and Sulfur and the Related Elements* 20(2):139-44 (1984).
Balia et al., *Indian J. Chem.* 9(3):220-5 (1971).
CA:110:74956 abs of Org Prep Proced Int by VR Balasubramanyan 20(3) pp. 205-212 1988.
CA:126:185889 abs of JP 09003037 Jan. 7, 1997.
Reddy et al., *Org. Prep. Proc. Int.*, 20(3):205-212 (1988).
Reddy et al., *Sulfur Lett.*, 13(2):83-90 (1991).
Reddy and Reddy, *Acta Chim. Acad. Sci. Hung.*,115(3):269-271 (1984).
Reddy et al., *Phosphorus, Sulfur Silicon Relat. Elem.*, 60:209-214 (1991).
Reddy and Reddy, *Acta Chim. Acad. Sci. Hung.*, 120(4):275-280 (1985).
Reddy and Reddy, *Synthesis* No. 4, 322-323 (1984).
Reddy et al., *Sulfur Lett.*, 7(2):43-48 (1987).
Reddy et al. *Phosphorus, Sulfur, and Silicon*, 53(1-4):285-290 (1990).
Makosza and Krylova, *Liebigs Ann./Recueil*, 2337-2340 (1997).
Reddy et al., *Acta Chim. Hung.*, 131(1):83-92 (1994).
CA:124:175763, abs of Reddy et al., *Indian J. Heterocycl. Chem.*, (1995), 5(1), 11-14.
CA:124:146025, abs of Reddy et al., *Indian J. Heterocycl. Chem.* (1995), 4(4), 259-264.
CA:126:166162, abs of Thompson et al., *Cancer Res.*, (1997) 57(2), 267-271.
Benati, et al., *J. Org. Chem.*, 59:2818-2823 (1994).
CA:120:323356 abs of Reddy et al., *Sulf. Lett.* (1993), 16(5-6), 227-35.
CA:122:132682 abs of Reddy et al., *Phosphorus, Sulfur Silicon Relat. Elem.* (1994), 90(1-4), 1-10.
CA:124:8731 abs of Reddy et al., *Indian J. Chem. Sect. B: Org. Chem. Incl. Med. Chem.* (1995) 34B(9), 816-22.

(Continued)

*Primary Examiner*—Johann Richter
*Assistant Examiner*—Chukwuma Nwaonicha
(74) *Attorney, Agent, or Firm*—Drinker Biddle & Reath LLP; Daniel A. Monaco

(57) ABSTRACT

(E)-styryl benzylsulfones of formula I are useful as anticancer agents:

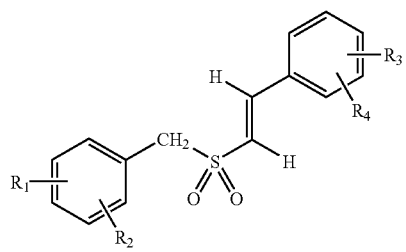

wherein $R_1$, $R_2$, $R_3$, and $R_4$ are as defined herein.

8 Claims, No Drawings

OTHER PUBLICATIONS

CA:76:121420 abs of Findlay et al. *Brit. J. Dermatol., Suppl.* (1971), No. 7, 44-9.

CA:105:133446 abs of Naidu et al., *Proc. Indian Acad. Sci., Chem Sci* (1985), 95(4), 391-5.

CA:126:185889 abs of Japanese Pat. App. 09-03,037 (Jan. 7, 1997).

CA:132:263142 abs of Hillaire et al., *Pathol. Biol.* (1999), 47(9), 895-902.

CA:130:336836 abs of Olson, *Med. Hypotheses* (1999), 51(6), 493-498.

CA:127:33922 abs of Evans and Taylor, *Tetrahedron Lett.* (1997), 3055-3058.

CA:125:327911 abs of Riad et al., *Egypt J. Chem.* (1996), 39(4), 353-364.

CA:120:210378 abs of Cheng and Hwang, *J. Chin. Biochem. Soc.* (1993), 22(1), 27-35.

CA:103:141088 abs of Janczewski and Ksiezopolski, *Pol. J. Chem.* (1984), 58(1-2-3), 103-16.

CA:121:256180 abs of Li et al.; *Bioorg. Med. Chem. Lett.* (1994), 4(13), 1585-90.

Tanaka et al., *Agric. Biol. Chem.* 41, 1953-1959, (1977).

CA:123:198103 abs of Riad et al., *Egypt J. Chem.* (1994) 37(2), 157-71.

\* cited by examiner

(E)-STYRYL SULFONE ANTICANCER AGENTS

CROSS-REFERENCE TO RELATED APPLICATIONS

This application is a continuation of U.S. patent application Ser. No. 09/937,684, filed Sep. 28, 2001 now U.S. Pat. No. 6,762,207, which is a 371 of PCT/US00/08565, filed Mar. 31, 2000, which claims the benefit of the filing dates of provisional applications Ser. Nos. 60/127,683, filed Apr. 2, 1999 and 60/143,975, filed Jul. 15, 1999. The entire disclosures of the aforesaid applications are incorporated herein by reference.

FIELD OF THE INVENTION

The invention relates to compositions and methods for the treatment of cancer.

BACKGROUND OF THE INVENTION

Extracellular signals received at transmembrane receptors are relayed into the cells by the signal transduction pathways (Pelech et al., *Science* 257:1335 (1992)) which have been implicated in a wide array of physiological processes such as induction of cell proliferation, differentiation or apoptosis (Davis et al., *J. Biol. Chem.* 268:14553 (1993)). The Mitogen Activated Protein Kinase (MAPK) cascade is a major signaling system by which cells transduce extracellular cues into intracellular responses (Nishida et al., *Trends Biochem. Sci.* 18:128 (1993); Blumer et al., *Trends Biochem. Sci.* 19:236 (1994)). Many steps of this cascade are conserved, and homologous for MAP kinases have been discovered in different species.

In mammalian cells, the Extracellular-Signal-Regulated Kinases (ERKs), ERK-1 and ERK-2 are the archetypal and best-studied members of the MAPK family, which all have the unique feature of being activated by phosphorylation on threonine and tyrosine residues by an upstream dual specificity kinase (Posada et al., *Science* 255:212 (1992); Biggs III et al., *Proc. Natl. Acad. Sci. USA* 89:6295 (1992); Garner et al., *Genes Dev.* 6:1280 (1992)).

Recent studies have identified an additional subgroup of MAPKs, known as c-Jun NH2-terminal kinases 1 and 2 (JNK-1 and JNK-2), that have different substrate specificities and are regulated by different stimuli (Hibi et al., *Genes Dev.* 7:2135 (1993)). JNKs are members of the class of stress-activated protein kinases (SPKs). JNKs have been shown to be activated by treatment of cells with UV radiation, pro-inflammatory cytokines and environmental stress (Derijard et al., *Cell* 1025 (1994)). The activated JNK binds to the amino terminus of the c-Jun protein and increases the protein's transcriptional activity by phosphorylating it at ser63 and ser73 (Adler et al., *Proc. Natl. Acad. Sci. USA* 89:5341 (1992); Kwok et al., *Nature* 370:223 (1994)).

Analysis of the deduced primary sequence of the JNKs indicates that they are distantly related to ERKs (Davis, *Trends Biochem. Sci.* 19:470 (1994)). Both ERKs and JNKs are phosphorylated on Tyr and Thr in response to external stimuli resulting in their activation (Davis, *Trends Biochem. Sci.* 19:470 (1994)). The phosphorylation (Thr and Tyr) sites, which play a critical role in their activation are conserved between ERKs and JNKs (Davis, *Trends Biochem. Sci.* 19:470 (1994)). However, these sites of phosphorylation are located within distinct dual phosphorylation motifs: Thr-Pro-Tyr (JNK) and Thr-Glu-Tyr (ERK). Phosphorylation of MAPKs and JNKs by an external signal often involves the activation of protein tyrosine kinases (PTKs) (Gille et al., *Nature* 358:414 (1992)), which constitute a large family of proteins encompassing several growth factor receptors and other signal transducing molecules.

Protein tyrosine kinases are enzymes which catalyze a well defined chemical reaction: the phosphorylation of a tyrosine residue (Hunter et al., *Annu Rev Biochem* 54:897 (1985)). Receptor tyrosine kinases in particular are attractive targets for drug design since blockers for the substrate domain of these kinases is likely to yield an effective and selective antiproliferative agent. The potential use of protein tyrosine kinase blockers as antiproliferative agents was recognized as early as 1981, when quercetin was suggested as a PTK blocker (Graziani et al., *Eur. J. Biochem.* 135: 583–589 (1983)).

The best understood MAPK pathway involves extracellular signal-regulated kinases which constitute the Ras/Raf/MEK/ERK kinase cascade (Boudewijn et al., *Trends Biochem. Sci.* 20, 18 (1995)). Once this pathway is activated by different stimuli, MAPK phosphorylates a variety of proteins including several transcription factors which translocate into the nucleus and activate gene transcription. Negative regulation of this pathway could arrest the cascade of these events.

What are needed are new anticancer chemotherapeutic agents which target receptor tyrosine kinases and which arrest the Ras/Raf/MEK/ERK kinase cascade. Oncoproteins in general, and signal transducing proteins in particular, are likely to be more selective targets for chemotherapy because they represent a subclass of proteins whose activities are essential for cell proliferation, and because their activities are greatly amplified in proliferative diseases.

What is also needed are new anticancer therapeutics which are highly selective in the killing of tumor cells, but not normal cells.

SUMMARY OF THE INVENTION

It is an object of the invention to provide compounds, compositions and methods for the treatment of cancer and other proliferative diseases. The biologically active compounds are in the form of (E)-styryl benzylsulfones.

It is an object of the invention to provide compounds which are highly selective in killing tumor cells but not normal cells.

It is a further object of the invention to provide novel polymers prepared by polymerization of (E)-styryl benzylsulfones.

It is a further object of the invention to provide intermediates useful for the preparation of compounds having anticancer activity. The intermediates comprise (E)-styryl benzylsulfonyl acetic acids.

According to one embodiment of the invention, novel compounds are provided according to formula I:

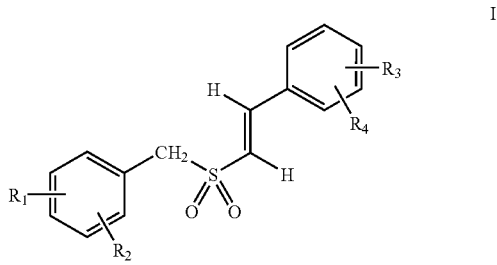

wherein:

$R_1$, $R_2$, $R_3$, and $R_4$ are independently selected from the group consisting of hydrogen; fluoro; chloro; bromo; C1–C6 alkyl; C1–C6 alkoxy; nitro; cyano; and trifluoromethyl;

with the proviso that
(a) $R_1$, $R_2$, $R_3$, and $R_4$ may not all be hydrogen;
(b) when $R_1$, $R_2$, and $R_3$ are hydrogen, then $R_4$ may not be:
  (i) 2- or 4-chloro or 4-fluoro;
  (ii) 2-nitro, 3-nitro or 4-nitro;
  (iii) 4-methoxy or 4-ethoxy; or
  (iv) 4-methyl;
(c) when $R_1$ and $R_3$ are hydrogen and $R_2$ is 4-chloro, then $R_4$ may not be 4-chloro, 4-fluoro, 4-bromo, 4-nitro, 4-isopropyl or 4-ethoxy;
(d) when $R_1$ and $R_3$ are hydrogen and $R_2$ is 4-fluoro, then $R_4$ may not be 4-fluoro, 4-bromo, or 4-chloro
(e) when $R_1$ and $R_3$ are hydrogen and $R_2$ is 4-nitro, then $R_4$ may not be 4-chloro, 4-nitro, 4-bromo, 4-fluoro, 4-methyl, or 4-methoxy;
(f) when $R_1$ and $R_3$ are hydrogen and $R_2$ is 4-methyl, $R_4$ may not be 4-chloro, 4-bromo, 4-fluoro, 4-methyl or 2-chloro;
(g) when $R_1$ and $R_3$ are hydrogen and $R_2$ is 4-bromo, then $R_4$ may not be 4-fluoro, 4-bromo or 4-chloro;
(h) when $R_1$ and $R_2$ are hydrogen, then $R_3$ and $R_4$ may not be 2,4-dichloro, 2,3-dimethoxy or 3,4-dimethoxy;
(i) when $R_1$ is hydrogen, then $R_2$, $R_3$ and $R_4$ may not all be fluoro; and
(j) when $R_1$ is hydrogen and $R_3$ is 2-fluoro, then $R_2$ and $R_4$ may not both be selected from the group consisting of 4-chloro, 4-bromo, and 4-fluoro.

According to a preferred embodiment of the invention, novel compounds are provided according to formula I wherein $R_1$, $R_2$, $R_3$, and $R_4$ are independently selected from the group consisting of hydrogen, chloro, fluoro, bromo, nitro, cyano and trifluoromethyl. According to a more preferred embodiment, $R_1$, $R_2$, $R_3$, and $R_4$ are independently selected from the group consisting of hydrogen, chloro, fluoro and bromo; most preferably hydrogen, chloro and fluoro.

In a further preferred embodiment, novel compounds are provided according to formula I wherein (1) at least one of $R_1$ and $R_2$ is other than hydrogen and is located at the 2-, 3- and/or 4-position of the phenyl ring to which it is attached, and is preferably selected from chloro and fluoro, most preferably chloro; and/or (2) wherein at least one of $R_3$ and $R_4$ is other than hydrogen and is located at the 2- and/or 4-position of the phenyl ring to which it is attached, and is preferably selected from chloro and fluoro. In other preferred embodiments wherein at least one of $R_1$ and $R_2$ is other than hydrogen, and at least one of $R_3$ and $R$ is other than hydrogen, (i) $R_2$ is 4-halogen or 4-cyano, and $R_4$ is 4-nitro; or (ii) $R_2$ is 4-C1–C6 alkoxy, and $R_4$ is 4-nitro or 4-halogen. $R_1$ and $R_3$ are preferably hydrogen in these embodiments.

In another embodiment of the invention, a pharmaceutical composition is provided comprising a pharmaceutically acceptable carrier and one or more compounds of formula II:

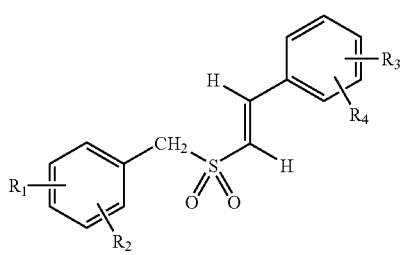

II wherein
$R_1$, $R_2$, $R_3$, and $R_4$ are independently selected from the group consisting of hydrogen; fluoro; chloro; bromo; C1-C6 alkyl; C1-C6 alkoxy; nitro; cyano; and trifluoromethyl;
with the proviso that
(a) $R_1$, $R_2$, and $R_3$ are not all hydrogen when $R_4$ is 2-chloro or 4-chloro;
(b) when $R_1$ and $R_3$ are hydrogen and $R_2$ is 4-bromo or 4-chloro, then $R_4$ may not be 4-chloro, 4-fluoro or 4-bromo;
(c) when $R_1$ and $R_3$ are hydrogen and $R_2$ is 4-fluoro, $R_4$ may not be 4-fluoro or 4-bromo;
(d) when $R_1$ is hydrogen, and $R_4$ is 2-fluoro, then $R_2$ and $R_3$ may not be 4-fluoro;
(e) when $R_1$ is hydrogen and $R_3$ is 4-hydrogen, 4-chloro, 4-bromo, 4-methyl or 4-methoxy, and $R_4$ is 2-hydrogen, 2-chloro or 2-fluoro; then $R_2$ may not be 4-hydrogen, 4-chloro, 4-fluoro or 4-bromo.

According to a related invention, novel compounds are provided according to formula III:

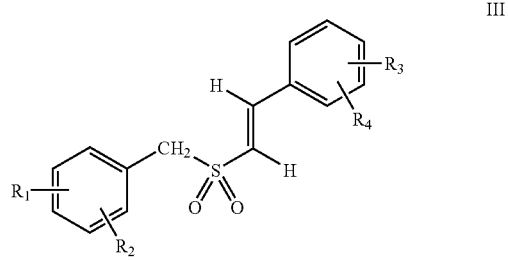

III wherein
$R_1$, $R_2$, $R_3$, and $R_4$ are independently selected from the group consisting of hydrogen; fluoro; chloro; bromo; iodo; C1–C6 alkyl; C1–C6 alkoxy; nitro; cyano; and trifluoromethyl;
provided at least one of $R_1$, $R_2$, $R_3$, and $R_4$ is iodo.

According to a preferred embodiment, at least one of $R_1$ and $R_2$ in formula III is other than hydrogen and is located at the 2- or 4-position of the phenyl ring to which it is attached; and at least one of $R_3$ and $R_4$ is other than hydrogen and is located at the 2- or 4-position of the phenyl ring to which it is attached. According to a further preferred embodiment, $R_2$ and $R_4$ in formula III are hydrogen, and $R_1$ and $R_3$ are located at the 4-position of the respective phenyl rings to which they are attached. According to a further preferred embodiment, one of $R_1$ or $R_3$ is selected from the group consisting of chloro, fluoro, bromo and nitro, the other of $R_1$ or $R_3$ being iodo.

A pharmaceutical composition is also provided comprising a pharmaceutically acceptable carrier and one or more compounds of formula III above, wherein $R_1$, $R_2$, $R_3$, and $R_4$ are defined as above for formula III.

Where $R_1$, $R_2$, $R_3$ or $R_4$ is an alkyl or alkoxy group in any compound of formulae I, II or III, the carbon chain may be branched or straight, with straight being preferred. Preferably, the alkyl and alkoxy groups comprise C1–C3 alkyl and C1–C4 alkoxy, most preferably methyl and methoxy.

According to another embodiment of the invention, a method of treating an individual for a proliferative disorder, particularly cancer, is provided, comprising administering to said individual an effective amount of a compound according to formula II or III, alone or in combination with a pharmaceutically acceptable carrier.

In another embodiment of the invention, a method of inhibiting growth of tumor cells in an individual afflicted with cancer is provided comprising administering to said individual an effective amount of a compound according to formula II or III, alone or in combination with a pharmaceutically acceptable carrier.

In another embodiment, a method of inducing apoptosis of cancer cells, more preferably tumor cells, in an individual afflicted with cancer is provided, comprising administering to said individual an effective amount of a compound according to formula II or III, alone or in combination with a pharmaceutically acceptable carrier.

In yet another embodiment of the present invention, benzyl sulfones having the structural formula II or III, may be utilized as monomers in the synthesis of a new class of polymers having pendant benzylsulfone groups.

The present invention also provides a series of substituted benzylsulfonyl acetic acid compounds having structural formula V, below. The substituted benzylsulfonyl acetic acid compounds are useful as intermediates in the synthesis of novel (E)-styryl benzylsulfone compounds of formula I, according to Method A, below.

DETAILED DESCRIPTION OF THE INVENTION

According to the present invention, certain (E)-styryl benzylsulfone derivatives selectively kill various tumor cell types without killing normal cells. Without wishing to be bound by any theory, it is believed that the compounds affect the MAPK signal transduction pathway, thereby affecting tumor cell growth and viability. This cell growth inhibition is associated with regulation of the ERK and JNK types of MAPK. Without wishing to be bound by any theory, the styryl sulfones of the present invention may block the phosphorylating capacity of ERK-2.

The compounds of the invention have been shown to inhibit the proliferation of tumor cells by inducing cell death. The compounds are believed effective against a broad range of tumor types, including but not limited to the following: breast, prostate, ovarian, lung, colorectal, brain (i.e., glioma) and renal. The compounds are also believed effective against leukemic cells. The compounds do not kill normal cells in concentrations at which tumor cells are killed.

The compounds are also useful in the treatment of non-cancer proliferative disorders, including but not limited to the following: hemangiomatosis in new born, secondary progressive multiple sclerosis, chronic progressive myelo-degenerative disease, neurofibromatosis, ganlioneuromatosis, keloid formation, Pagets Disease of the bone, fibrocystic disease of the breast, Peronies and Duputren's fibrosis, restenosis and cirrhosis.

Treatment of this broad range of tumor cells with the styryl benzylsulfone compounds of the invention leads to inhibition of cell proliferation and induction of apoptotic cell death. In breast tumors, the effect is observed for estrogen receptor (ER) positive as well as estrogen receptor negative cells.

Tumor cells treated with the compounds of the invention accumulate in the G2/M phase of the cell cycle. As the cells exit the G2/M phase, they appear to undergo apoptosis. Treatment of normal cells with the styryl sulfones does not result in apoptosis.

Synthesis of (E)-Styryl Benzylsulfones

The styryl benzylsulfones are characterized by cis-trans isomerism resulting from the presence of one or more double bonds. The compounds are named according to the Cahn-Ingold-Prelog system, the IUPAC 1974 Recommendations, Section E: Stereochemistry, in *Nomenclature of Organic Chemistry*, John Wiley & Sons, Inc., New York, N.Y., 4$^{th}$ ed., 1992, p. 127–138. Steric relations around a double bond are designated as "Z" or "E".

(E)-styryl benzylsulfones are prepared by Knoevenagel condensation of aromatic aldehydes with benzylsulfonyl acetic acids. The procedure is described by Reddy et al., *Acta. Chim. Hung.* 115:269 (1984); Reddy et al., *Sulfur Letters* 13:83 (1991); Reddy et al., *Synthesis* 322 (1984); and Reddy et al., *Sulfur Letters* 7:43 (1987), the entire disclosures of which are incorporated herein by reference.

The (E)-styryl benzylsulfones can be prepared according to either of the following Methods A and B:

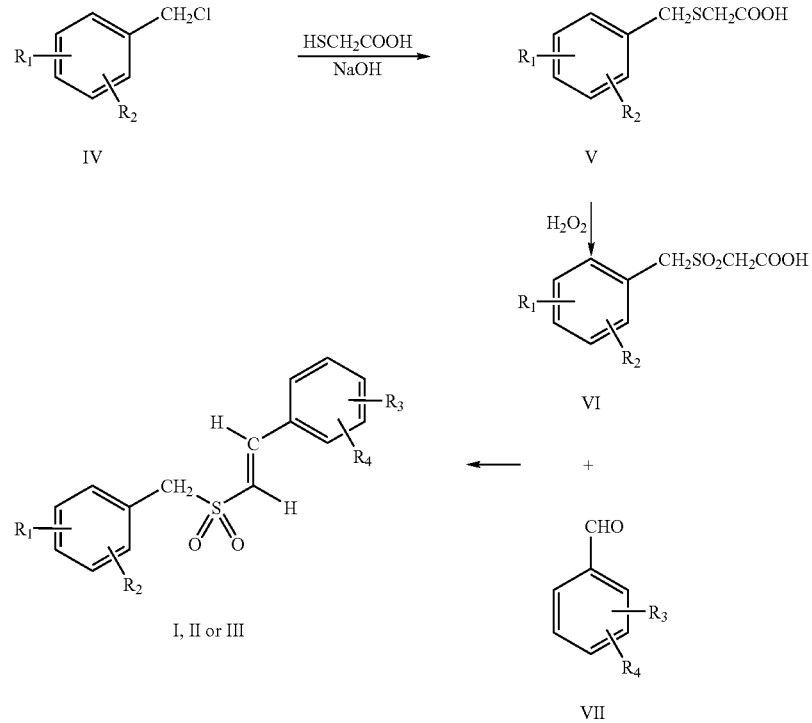

METHOD B

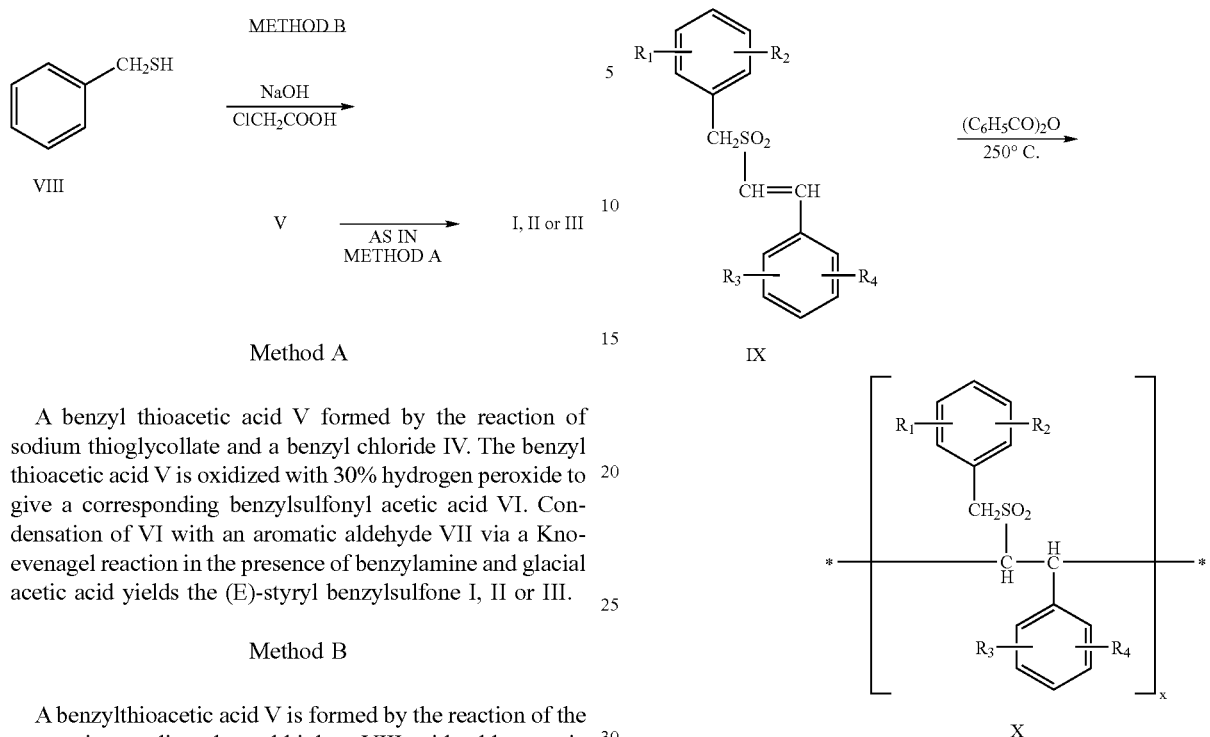

Method A

A benzyl thioacetic acid V formed by the reaction of sodium thioglycollate and a benzyl chloride IV. The benzyl thioacetic acid V is oxidized with 30% hydrogen peroxide to give a corresponding benzylsulfonyl acetic acid VI. Condensation of VI with an aromatic aldehyde VII via a Knoevenagel reaction in the presence of benzylamine and glacial acetic acid yields the (E)-styryl benzylsulfone I, II or III.

Method B

A benzylthioacetic acid V is formed by the reaction of the appropriate sodium benzylthiolate VIII with chloroacetic acid. Oxidation of V to the corresponding benzylsulfonyl acetic acid VI and subsequent Knoevenagel condensation with aldehyde VII is carried out as in Method A.

Substituted benzylsulfonyl acetic acid compounds Va, Vb, Vc, and Vd according to formula V were prepared by reacting the corresponding benzyl chloride with thioglycolic acid under basic conditions (Method A). These compounds are novel intermediates.

| No. | Compound | $R_1$ | $R_2$ | M.P.(° C.) |
|---|---|---|---|---|
| Va | 4-nitrobenzylsulfonyl acetic acid | H | 4-$NO_2$ | 165–166 |
| Vb | 4-trifluoromethylbenzyl-sulfonyl acetic acid | H | 4-$CF_3$ | 164–165 |
| Vc | 2,4-dichlorobenzyl-sulfonyl acetic acid | 2-Cl | 4-Cl | 165–166 |
| Vd | 3,4-dichlorobenzyl-sulfonyl acetic acid | 3-Cl | 4-Cl | 132–134 |

(E)-Styryl benzylsulfones may be utilized as monomers in the synthesis of polymers X having pendant aryl and benzylsulfone groups. The polymerization of styryl benzylsulfones defined according to formula IX below into formula X polymers is accomplished by heating the formula IX compound above 250° C. in the presence of a free radical initiator. The initiator may comprise benzoyl peroxide, for example:

The degree of polymerization in the polymer of formula X, "x", may range from about 10 to about 150, providing an oligomer or polymer of from 5,000 to 50,000 daltons. Other degrees of polymerization are also contemplated. $R_1$, $R_2$, $R_3$, and $R_4$ in the monomer of formula IX, and in the polymer of formula X, are independently selected from the group consisting of hydrogen; halogen, i.e., fluoro, chloro, bromo and iodo, most preferably fluoro, chloro and bromo; C1–C6 alkyl; C1–C6 alkoxy; nitro; cyano; and trifluoromethyl.

The (E)-styryl benzylsulfones may be derivatized with a chemical group to permit conjugation to a carrier molecule, for the purpose of raising antibodies to the styryl sulfones. Suitable derivatizing chemistries are well-known to those skilled in the art. Preferably, the derivative comprises a carboxylic acid derivative. The carrier may comprise any molecule sufficiently large to be capable of generating an immune response in an appropriate host animal. One such preferred carrier is keyhole limpet haemocyanin (KLH).

Therapeutic Administration

The (E)-styryl benzylsulfones of the invention may be administered in the form of a pharmaceutical composition, in combination with a pharmaceutically acceptable carrier. The active ingredient in such formulations may comprise from 0.1 to 99.99 weight percent. By "pharmaceutically acceptable carrier" is meant any carrier, diluent or excipient which is compatible with the other ingredients of the formulation and to deleterious to the recipient.

The compounds of the invention may be administered to individuals (mammals, including animals and humans) afflicted with cancer. The compounds are also useful in the treatment of non-cancer proliferative disorders, that is, proliferative disorders which are characterized by benign indications. Such disorders may also be known as "cytoproliferative" or "hyperproliferative" in that cells are made by the body at an atypically elevated rate. Such disorders include, but are not limited to, the following: hemangiomatosis in new born, secondary progressive multiple sclerosis, chronic progressive myelodegenerative disease, neurofibromatosis, ganglioneuromatosis, keloid formation, Pagets Disease of the bone, fibrocystic disease of the breast, Peronies and Duputren's fibrosis, restenosis and cirrhosis.

The compounds may be administered by any route, including oral and parenteral administration. Parenteral administration includes, for example, intravenous, intramuscular, intraarterial, intraperitoneal, intranasal, rectal, intravaginal, topical or subcutaneous administration. The active agent is preferably administered with a pharmaceutically acceptable carrier selected on the basis of the selected route of administration and standard pharmaceutical practice.

The active agent may be formulated into dosage forms according to standard practices in the field of pharmaceutical preparations. See Gennaro Alphonso, ed., *Remington's Pharmaceutical Sciences*, 18th Ed., (1990) Mack Publishing Co., Easton, Pa. Suitable dosage forms may comprise, for example, tablets, capsules, solutions, parenteral solutions, troches, suppositories, or suspensions.

For parenteral administration, the active agent may be mixed with a suitable carrier or diluent such as water, an oil (particularly a vegetable oil), ethanol, saline solution, aqueous dextrose (glucose) and related sugar solutions, glycerol, or a glycol such as propylene glycol or polyethylene glycol. Solutions for parenteral administration preferably contain a water soluble salt of the active agent. Stabilizing agents, antioxidizing agents and preservatives may also be added. Suitable antioxidizing agents include sulfite, ascorbic acid, citric acid and its salts, and sodium EDTA. Suitable preservatives include benzalkonium chloride, methyl- or propylparaben, and chlorbutanol. The composition for parenteral administration may take the form of an aqueous or nonaqueous solution, dispersion, suspension or emulsion.

For oral administration, the active agent may be combined with one or more solid inactive ingredients for the preparation of tablets, capsules, pills, powders, granules or other suitable oral dosage forms. For example, the active agent may be combined with at least one excipient such as fillers, binders, humectants, disintegrating agents, solution retarders, absorption accelerators, wetting agents absorbents or lubricating agents. According to one tablet embodiment, the active agent may be combined with carboxymethylcellulose calcium, magnesium stearate, mannitol and starch, and then formed into tablets by conventional tableting methods.

The specific dose of compound according to the invention to obtain therapeutic benefit will, of course, be determined by the particular circumstances of the individual patient including, the size, weight, age and sex of the patient, the nature and stage of the disease, the aggressiveness of the disease, and the route of administration. For example, a daily dosage of from about 0.05 to about 50 mg/kg/day may be utilized. Higher or lower doses are also contemplated.

EXAMPLES

General Procedure for Synthesis (E)-Styryl Benzylsulfones

Part A. To a solution of (8 g, 0.2 mol) sodium hydroxide in methanol (200 ml), thioglycolic acid (0.1 mol) is added slowly and the precipitate formed is dissolved by stirring the contents of the flask. Then an appropriately substituted or unsubstituted benzyl chloride (0.1 mol) is added stepwise and the reaction mixture is refluxed for 2–3 hours. The cooled contents are poured onto crushed ice and neutralized with dilute hydrochloric acid (200 ml). The resulting corresponding benzylthioacetic acid (0.1 mol) is subjected to oxidation with 30% hydrogen peroxide (0.12 mol) in glacial acetic acid (125 ml) by refluxing for 1 hour. The contents are cooled and poured onto crushed ice. The separated solid is recrystallized from hot water to give the corresponding pure benzylsulfonylacetic acid.

Part B. A mixture of the benzylsulfonyl acetic acid (10 mmol), an appropriately substituted or unsubstituted aromatic aldehyde (10 mmol), and benzylamine (200 µl) in glacial acetic acid (12 ml) is refluxed for 2–3 hours. The contents are cooled and treated with cold ether (50 ml). Any product precipitated out is separated by filtration. The filtrate is diluted with more ether and washed successively with a saturated solution of sodium bicarbonate (20 ml), sodium bisulfite (20 ml), dilute hydrochloric acid (20 ml) and finally with water (35 ml). Evaporation of the dried ethereal layer yields styryl benzylsulfones as a solid material.

In each of the following examples, the substituted benzylsulfonyl acetic acid was made according to Part A of the General Procedure. All the styryl benzylsulfone compounds were recrystallized from 2-propanol and the purity was checked by thin layer chromatography.

Example 1

(E)-4-Fluorostyryl-4-trifluoromethylbenzylsulfone

A solution of 4-trifluorobenzylsulfonylacetic acid (10 mmol) and 4-fluorobenzaldehyde (10 mmol) was subjected to the General Procedure, Part B. The title compound melting point 166–168° C., was obtained in 82% yield.

Example 2

(E)-4-Chlorostyryl-4-trifluoromethylbenzylsulfone

A solution of 4-trifluoromethylbenzylsulfonylacetic acid (10 mmol) and 4-chlorobenzaldehyde (10 mmol) was subjected to the General Procedure, Part B. The title compound, melting point 164–168° C., was obtained in 88% yield.

Example 3

(E)-4-Bromostyryl-4-trifluoromethylbenzylsulfone

A solution of 4-trifluoromethylbenzylsulfonylacetic acid (10 mmol) and 4-bromobenzaldehyde (10 mmol) was subjected to the General Procedure, Part B. The title compound, melting point 181–183° C., was obtained in 85% yield.

Example 4

(E)-4-Fluorostyryl-2,4-dichlorobenzylsulfone

A solution of 2,4-dichlorobenzylsulfonyl acid (10 mmol) and 4-fluorobenzaldehyde (10 mmol) was subjected to the General Procedure, Part B. The title compound, melting point 146–148° C., was obtained in 78% yield.

Example 5

(E)-4-Chlorostyryl-2,4-dichlorobenzylsulfone

A solution of 2,4-dichlorobenzylsulfonylacetic acid (10 mmol) and 4-chlorobenzaldehyde (10 mmol) was subjected to the General Procedure, Part B. The title compound, melting point 148–149° C., was obtained in 84% yield.

Example 6

(E)-4-Fluorostyryl-3,4-dichlorobenzylsulfone

A solution of 3,4-dichlorobenzylsulfonylacetic acid (10 mmol) and 4-fluorobenzaldehyde (10 mmol) was subjected to the General Procedure, Part B. The title compound, melting point 120–122° C., was obtained in 82% yield.

Example 7

(E)-4-Chlorostyryl-3,4-dichlorobenzylsulfone

A solution of 3,4-dichlorobenzylsulfonylacetic acid (10 mmol) and 4-chlorobenzaldehyde (10 mmol) was subjected to the General Procedure, Part B. The title compound, melting point 149–151° C., was obtained in 86% yield.

Example 8

(E)-4-Bromostyryl-3,4-dichlorobenzylsulfone

A solution of 3,4-dichlorobenzylsulfonylacetic acid (10 mmol) and 4-bromobenzaldehyde (10 mmol) was subjected to the General Procedure, Part B. The title compound, melting point 154–155° C., was obtained in 84% yield.

Example 9

(E)-4-Fluorostyryl-4-nitrobenzylsulfone

A solution of 4-nitrobenzylsulfonylacetic acid (10 mmol) and 4-fluorobenzaldehyde (10 mmol) was subjected to the General Procedure, Part B. The title compound, melting point 160–161° C., was obtained in 76% yield.

Example 10

(E)-4-Fluorostyryl-4-cyanobenzylsulfone

A solution of 4-cyanobenzysulfonylacetic acid (10 mmol) and 4-fluorobenzaldehyde (10 mmol) was subjected to the General Procedure Part B. The title compound, melting point 150–151° C., was obtained in 82% yield.

Example 11

(E)-4-Chlorostyryl-4-cyanobenzylsulfone

A solution of 4-cyanobenzylsulfonyl acetic acid (10 mmol) and 4-chlorobenzaldehyde (10 mmol) was subjected to the General Procedure, Part B. The title compound, melting point 173–177° C., was obtained in 86% yield.

Example 12

(E)-4-Bromostyryl-4-cyanobenzylsulfone

A solution of 4-cyanobenzylsulfonyl acetic acid (10 mmol) and 4-bromobenzaldehyde (10 mmol) was subjected to the General Procedure, Part B. The title compound, melting point 183–184° C., was obtained in 77% yield.

Example 13

(E)-3,4-Difluorostyryl-4-chlorobenzylsulfone

A solution of 4-chlorobenzylsulfonyl acetic acid (10 mmol) and 3,4 difluorobenzaldehyde was subjected to the General Procedure, Part B. The title compound, melting point 204–205° C., was obtained in 73% yield.

Example 14

(E)-3-Chloro-4-fluorostyryl-4-chlorobenzylsulfone

A solution of 4-chlorobenzylsulfonylacetic acid (10 mmol) and 3-chloro-4-fluorobenzaldehyde was subjected to the General Procedure, Part B. The title compound, melting point 181–183° C., was obtained in 78% yield.

Example 15

(E)-2-Chloro-4-fluorostyryl-4-chlorobenzylsulfone

A solution of 4-chlorobenzylsulfonylacetic acid (10 mmol) and 2-chloro-4-fluorobenzaldehyde was subjected to the General Procedure, Part B. The title compound, melting point 149–150° C., was obtained in 68% yield.

Example 16

(E)-2,4-Dichlorostyryl-4-chlorobenzylsulfone

A solution of 4-chlorobenzylsulfonylacetic acid (10 mmol) and 2,4-dichlorobenzaldehyde was subjected to the General Procedure, Part B. The title compound, melting point 164–165° C., was obtained in 78% yield.

Example 17

(E)-3,4-Dichlorostyryl-4-chlorobenzylsulfone

A solution of 4-chlorobenzylsulfonyl acetic acid (10 mmol) and 3,4-dichlorobenzaldehyde (10 mmol) was subjected to the General procedure, Part B. The title compound, melting point 170–171° C., was obtained in 73% yield.

Example 18

(E)-2,3-Dichlorostyryl-4-chlorobenzylsulfone

A solution of 4-chlorobenzylsulfonyl acetic acid (10 mmol) and 2,3-dichlorobenzaldehyde (10 mmol) was subjected to the General Procedure, part B. The title compound, melting point 170–171° C., was obtained in 72% yield.

Example 19

(E)-4-Fluorostyryl-4-iodobenzylsulfone

A solution of 4-iodobenzylsulfonyl acetic acid (10 mmol) and 4-fluorobenzaldehyde (10 mmol) was subjected to the General Procedure, part B. The title compound, melting point 171–173° C., was obtained in 98% yield. ($^1$HNMR, $CDCl_3$) d 4.27(s, $CH_2$), 6.60 (d, =CH, J=15.7 Hz), 7.18–7.80 (m, 9H, Aroma+=CH).

Example 20

(E)-4-Iodostyryl-4-fluorobenzylsulfone

A solution of 4-fluorobenzylsulfonyl acetic acid (10 mmol) and 4-iodobenzaldehyde (10 mmol) was subjected to the General Procedure, part B. The title compound, melting point 168–170° C., was obtained in 58% yield.

Example 21

(E)-4-Iodostyryl-4-chlorobenzylsulfone

A solution of 4-chlorobenzylsulfonyl acetic acid (10 mmol) and 4-iodobenzaldehyde (10 mmol) was subjected to the General Procedure, part B. The title compound, melting point 181–182° C., was obtained in 70% yield. ($^1$HNMR, CDCl$_3$) d 4.27(s, CH$_2$), 6.60 (d, =CH, J=15.7 Hz), 7.18–7.80 (m, 9H, Aroma+=CH).

Example 22

(E)-4-Iodostyryl-4-bromobenzylsulfone

A solution of 4-bromobenzylsulfonyl acetic acid (10 mmol) and 4-iodobenzaldehyde (10 mmol) was subjected to the General Procedure, part B. The title compound, melting point 201–203° C., was obtained in 71% yield.

Example 23

(E)-4-Chlorostyryl-4-iodobenzylsulfone

A solution of 4-iodobenzylsulfonyl acetic acid (10 mmol) and 4-chlorobenzaldehyde (10 mmol) was subjected to the General Procedure, part B. The title compound, melting point 200–202° C., was obtained in 86% yield. ($^1$HNMR, CDCl$_3$) d 4.27(s, CH$_2$), 6.60 (d, =CH, J=15.7 Hz), 7.18–7.80 (m, 9H, Aroma+=CH).

Example 24

(E)-4-Bromostyryl-4-iodobenzylsulfone

A solution of 4-iodobenzylsulfonyl acetic acid (10 mmol) and 4-bromobenzaldehyde (10 mmol) was subjected to the General Procedure, part B. The title compound, melting point 217–219° C., was obtained in 88% yield.

Example 25

(E)-2-Nitrostyryl-4-iodobenzylsulfone

A solution of 4-iodobenzylsulfonyl acetic acid (10 mmol) and 2-nitrobenzaldehyde (10 mmol) was subjected to the General Procedure, part B. The title compound, melting point 227–229° C., was obtained in 62% yield.

Example 26

(E)-4-Nitrostyryl-4-iodobenzylsulfone

A solution of 4-iodobenzylsulfonyl acetic acid (10 mmol) and 4-nitrobenzaldehyde (10 mmol) was subjected to the General Procedure, part B. The title compound, melting point 227–228° C., was obtained in 62% yield.

Example 27

(E)-4-Iodostyryl-4-methoxybenzylsulfone

A solution of 4-methoxybenzylsulfonyl acetic acid (10 mmol) and 4-iodobenzaldehyde (10 mmol) was subjected to the General Procedure, part B. The title compound, melting point 201–203° C., was obtained in 56% yield.

Example 28

(E)-4-Iodostyryl-2,4-dichlorobenzylsulfone

A solution of 2,4-dichlorobenzylsulfonyl acetic acid (10 mmol) and 4-iodobenzaldehyde (10 mmol) was subjected to the General Procedure, part B. The title compound, melting point 181–182° C., was obtained in 60% yield.

The following additional compounds In Table 1 were prepared according to the same synthetic methods (M.P.=melting point):

TABLE 1

| Ex. | M.P. (° C.) | Yield (%) | Compound |
|---|---|---|---|
| 29 | 134–136 | 55 | (E)-2-nitrostyryl-4-fluorobenzylsulfone |
| 30 | 170–173 | 64 | (E)-3-nitrostyryl-4-fluorobenzylsulfone |
| 31 | 151–152 | 61 | (E)-4-nitrostyryl-4-fluorobenzylsulfone |
| 32 | 96–98 | 54 | (E)-2-trifluoromethylstyryl-4-fluorobenzylsulfone |
| 33 | 117–119 | 55 | (E)-3-trifluoromethylstyryl-4-fluorobenzylsulfone |
| 34 | 125–128 | 73 | (E)-4-trifluoromethytstyryl-4-fluorobenzylsulfone |
| 35 | 108–112 | 52 | (E)-2-trifluoromethy-4-fluorostyryl-4-fluoro-benzylsulfone |
| 36 | 128–132 | 58 | (E)-2-nitrostyryl-4-chlorobenzylsulfone |
| 37 | 156–157 | 60 | (E)-3-nitrostyryl-4-chlorobenzylsulfone |
| 38 | 189–191 | 61 | (E)-4-nitrostyryl-4-chlorobenzylsulfone |
| 39 | 100–101 | 55 | (E)-2-trifluoromethylstyryl-4-chlorobenzylsulfone |
| 40 | 155–157 | 58 | (E)-3-trifluoromethylstyryl-4-chlorobenzylsulfone |
| 41 | 164–166 | 59 | (E)-4-trifluoromethylstyryl-4-chlorobenzylsulfone |
| 42 | 115–117 | 63 | (E)-2-trifluoromethyl-4-fluorostyryl-4-chloro-benzylsulfone |
| 43 | 169–171 | 63 | (E)-3-methyl-4-fluorostyryl-4-chlorobenzyl-sulfone |
| 44 | 136–138 | 57 | (E)-2-nitrostyryl-2,4-dichlorobenzylsulfone |
| 45 | 136–138 | 57 | (E)-2-trifluoromethyl-4-fluorostyryl-2,4-dichlorobenzylsulfone |
| 46 | 131–132 | 63 | (E)-2-nitrostyryl-4-bromobenzylsulfone |
| 47 | 168–170 | 56 | (E)-3-nitrostyryl-4-bromobenzylsulfone |
| 48 | 205–207 | 67 | (E)-4-nitrostyryl-4-bromobenzylsulfone |
| 49 | 102–104 | 57 | (E)-2-trifluoromethylstyryl-4-bromobenzylsulfone |
| 50 | 160–161 | 55 | (E)-3-trifluoromethylstyryl-4-fluorobenzylsulfone |
| 51 | 174–175 | 62 | (E)-4-trifluoromethylstyryl-4-bromoyano-benzylsulfone |
| 52 | 167–168 | 63 | (E)-2-nitrostyryl-4-cyanobenzylsulfone |
| 53 | 192–193 | 62 | (E)-3-nitrostyryl-4-cyanobenzylsulfone |
| 54 | 219–220 | 66 | (E)-4-nitrostyryl-4-cyanobenzylsulfone |
| 55 | 182–184 | 70 | (E)-4-fluorostyryl-4-methylbenzylsulfone |
| 56 | 191–192 | 70 | (E)-4-bromostyryl-4-methylbenzylsulfone |
| 57 | 128–130 | 51 | (E)-2-nitrostyryl-4-methylbenzylsulfone |
| 58 | 201–203 | 56 | (E)-3-nitrostyryl-4-methylbenzylsulfone |
| 59 | 194–195 | 57 | (E)-4-nitrostyryl-4-methylbenzylsulfone |
| 60 | 148–149 | 60 | (E)-4-fluorostyryl- 4-methoxybenzylsulfone |
| 61 | 176–177 | 66 | (E)-4-chlorostyryl-4-methoxybenzylsulfone |
| 62 | 179–181 | 60 | (E)-4-bromostyryl-4-methoxybenzylsulfone |
| 63 | 127–129 | 57 | (E)-2-nitrostyryl-4-methoxybenzylsulfone |
| 64 | 153–155 | 59 | (E)-3-nitrostyryl-4-methoxybenzylsulfone |
| 65 | 179–181 | 56 | (E)-4-nitrostyryl-4-methoxybenzylsulfone |
| 66 | 176–177 | 66 | (E)-4-chlorostyryl-4-nitrobenzylsulfone |
| 67 | 199–200 | 60 | (E)-4-fluorostyryl-4-nitrobenzylsulfone |

Effect of (E)-Styryl Benzylsulfones on Breast, and Prostate Tumor Cell Lines A. Cells.

The effect of the (E)-styryl benzylsulfones on normal fibroblasts and on tumor cells of breast, and prostate origin was examined utilizing one or more of the following cell lines: breast tumor cell lines MCF-7 and BT-20; prostate tumor cell line DU-145; colorectal carcinoma cell line DLD-1; non-small cell lung carcinoma cell line H157; and NIH/3T3 and HFL cells. MCF-7 is estrogen-responsive, while BT-20 is an estrogen-unresponsive cell line. NIH/3T3 and HFL are normal murine and human fibroblasts, respectively. MCF-7, BT-20, DLD-1 and H157 were grown in Dulbecco's modified Eagle's medium (DMEM) containing 10% fetal bovine serum supplemented with penicillin and streptomycin. DU145 was cultured in RPMI with 10% fetal bovine serum containing penicillin and streptomycin. NIH3T3 and HFL cells were grown in DMEM containing 10% calf serum supplemented with penicillin and streptomycin. All cell cultures were maintained at 37° C. in a humidified atmosphere of 5% $CO_2$.

B. Treatment with (E)-Styryl Sulfones and Viability Assay

Cells were treated with test compound at 2.5 mM concentration and cell viability was determined after 96 hours by the Trypan blue exclusion method. The results are set forth in Table 2. Activity for each compound is reported as a range of cell induced death (% Death) with the lowest activity in the range of 5–10% and the highest being above 80%.

Normal cells HFL and NIH 3T3 were treated with the same compounds in Table 2 under the same conditions of concentration and time. The normal cells displayed 5% growth inhibition but no appreciable cell death.

TABLE 2

Effect of (E)-styryl benzylsulfones on tumor cells

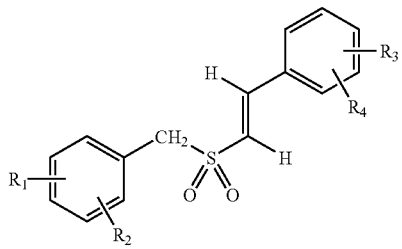

| | | | | | Tumor cell type | | | | |
|---|---|---|---|---|---|---|---|---|---|
| Ex | $R_1$ | $R_2$ | $R_3$ | $R_4$ | MCF-7 | DU145 | DLD-1 | H157 | BT20 |
| 1 | 4-$CF_3$ | H | 4-F | H | +++ | +++ | +++ | ++ | +++ |
| 2 | 4-$CF_3$ | H | 4-Cl | H | ++ | ++ | ++ | ND | ++ |
| 3 | 4-$CF_3$ | H | 4-Br | H | ND | + | + | ND | ++ |
| 4 | 2-Cl | 4-Cl | 4-F | H | ++ | ++ | ND | + | ++ |
| 5 | 2-Cl | 4-Cl | 4-Cl | H | +++ | + | ++ | ++ | ND |
| 6 | 3-Cl | 4-Cl | 4-F | H | ++++ | ++++ | ND | ND | ++++ |
| 7 | 3-Cl | 4-Cl | 4-Cl | H | ND | − | ND | ND | ++ |
| 8 | 3-Cl | 4-Cl | 4-Br | H | ND | − | − | ND | − |
| 9 | 4-$NO_2$ | H | 4-F | H | ++ | ++ | − | ++ | ++ |
| 10 | 4-CN | H | 4-F | H | +++ | ++ | ND | +++ | ND |
| 11 | 4-CN | H | 4-Cl | H | + | + | ND | + | ND |
| 12 | 4-CN | H | 4-Br | H | − | − | − | + | ND |
| 13 | 4-Cl | H | 3-F | 4-F | − | − | − | − | ND |
| 14 | 4-Cl | H | 3-Cl | 4-F | − | − | − | − | ND |
| 15 | 4-Cl | H | 2-Cl | 4-F | +++++ | +++++ | +++++ | +++++ | ND |
| 16 | 4-Cl | H | 2-Cl | 4-Cl | +++ | +++ | ++++ | ND | ND |
| 17 | 4-Cl | H | 3-Cl | 4-Cl | + | + | + | ND | ND |
| 18 | 4-Cl | H | 2-Cl | 3-Cl | + | + | + | ND | ND |
| 19 | 4-I | H | 4-F | H | ND | +++++ | +++++ | +++++ | +++++ |
| 20 | 4-F | H | 4-I | H | ND | ND | ND | ND | ND |
| 21 | 4-Cl | H | 4-I | H | ND | ++ | ++ | ++ | ++ |
| 22 | 4-Br | H | 4-I | H | ND | ++ | ++ | ++ | ++ |
| 23 | 4-I | H | 4-Cl | H | ND | ++ | ++ | ++ | +++ |
| 24 | 4-I | H | 4-Br | H | ND | ND | ND | ND | ND |
| 25 | 4-I | H | 2-$NO_2$ | H | ND | ++ | ++ | ++ | ++ |
| 26 | 4-I | H | 4-$NO_2$ | H | ND | ND | ND | ND | ND |
| 27 | 4-$CH_3O$ | H | 4-I | H | ND | ND | ND | ND | ND |
| 28 | 4-Cl | 2-Cl | 4-I | H | ND | ND | ND | ND | ND |
| 29 | 4-F | H | 2-$NO_2$ | H | ND | + | + | + | + |
| 30 | 4-F | H | 3-$NO_2$ | H | ND | + | + | + | + |
| 31 | 4-F | H | 4-$NO_2$ | H | ND | ++++ | ++++ | ++++ | ++++ |
| 32 | 4-F | H | 2-$CF_3$ | H | ND | + | + | + | + |
| 33 | 4-F | H | 3-$CF_3$ | H | ND | + | + | + | + |
| 34 | 4-F | H | 4-$CF_3$ | H | ND | + | + | + | + |
| 35 | 4-F | H | 2-$CF_3$ | 4-F | ND | + | + | + | + |

TABLE 2-continued

Effect of (E)-styryl benzylsulfones on tumor cells

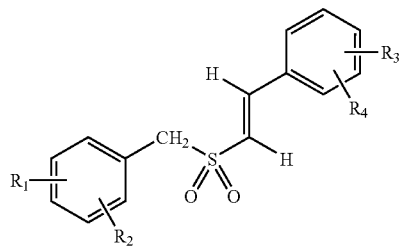

| Ex | $R_1$ | $R_2$ | $R_3$ | $R_4$ | MCF-7 | DU145 | DLD-1 | H157 | BT20 |
|---|---|---|---|---|---|---|---|---|---|
| 36 | 4-Cl | H | 2-$NO_2$ | H | ND | + | + | + | + |
| 37 | 4-Cl | H | 3-$NO_2$ | H | ND | + | + | + | + |
| 38 | 4-Cl | H | 4-$NO_2$ | H | ND | ++++ | ++++ | ++++ | ++++ |
| 39 | 4-Cl | H | 2-$CF_3$ | H | ND | + | + | + | + |
| 40 | 4-Cl | H | 3-$CF_3$ | H | ND | + | + | + | + |
| 41 | 4-Cl | H | 4-$CF_3$ | H | ND | + | + | + | + |
| 42 | 4-Cl | H | 4-F | 2-$CF_3$ | ND | + | + | + | + |
| 43 | 4-Cl | H | 4-F | 3-$CH_3$ | ND | + | + | + | + |
| 44 | 4-Cl | 2-Cl | 2-$NO_2$ | H | ND | + | + | + | + |
| 45 | 4-Cl | 2-Cl | 4-F | 2-$CF_3$ | ND | +++ | +++ | +++ | +++ |
| 46 | 4-Br | H | 2-$NO_2$ | H | ND | + | + | + | + |
| 47 | 4-Br | H | 3-$NO_2$ | H | ND | + | + | + | + |
| 48 | 4-Br | H | 4-$NO_2$ | H | ND | ++++ | ++++ | ++++ | ++++ |
| 49 | 4-Br | H | 2-$CF_3$ | H | ND | + | + | + | + |
| 50 | 4-Br | H | 3-$CF_3$ | H | ND | + | + | + | + |
| 51 | 4-Br | H | 4-$CF_3$ | H | ND | + | + | + | + |
| 52 | 4-CN | H | 2-$NO_2$ | H | ND | + | + | + | + |
| 53 | 4-CN | H | 3-$NO_2$ | H | ND | + | + | + | + |
| 54 | 4-CN | H | 4-$NO_2$ | H | ND | ++++ | ++++ | ++++ | ++++ |
| 55 | 4-$CH_3$ | H | 4-F | H | ND | + | + | + | + |
| 56 | 4-$CH_3$ | H | 4-Br | H | ND | + | + | + | + |
| 57 | 4-$CH_3$ | H | 2-$NO_2$ | H | ND | + | + | + | + |
| 58 | 4-$CH_3$ | H | 3-$NO_2$ | H | ND | + | + | + | + |
| 59 | 4-$CH_3$ | H | 4-$NO_2$ | H | ND | + | + | + | + |
| 60 | 4-$CH_3O$ | H | 4-F | H | ND | +++++ | +++++ | +++++ | +++++ |
| 61 | 4-$CH_3O$ | H | 4-Cl | H | ND | ++++ | ++++ | ++++ | ++++ |
| 62 | 4-$CH_3O$ | H | 4-Br | H | ND | ++++ | ++++ | ++++ | ++++ |
| 63 | 4-$CH_3O$ | H | 2-$NO_2$ | H | ND | + | + | + | + |
| 64 | 4-$CH_3O$ | H | 3-$NO_2$ | H | ND | + | + | + | + |
| 65 | 4-$CH_3O$ | H | 4-$NO_2$ | H | ND | ++++ | ++++ | ++++ | ++++ |
| 66 | 4-$NO_2$ | H | 4-Cl | H | ND | + | + | + | + |
| 67 | 4-$NO_2$ | H | 4-F | H | ND | + | + | + | + |

Cell death:
0% = −
5–10%: = +
10–15% = ++
40–50% = +++
50–60% = ++++
Above 80% = +++++
ND = not done Example 68

Conjugation of (E)-4-Fluorostyryl 4-chlorobenzylsulfone to Keyhole Limpet Haemocyanin A carboxylic acid derivative of (E)-4-fluorostyryl 4-chlorobenzylsulfone was synthesized by mixing 4-chlorobenzyl sulfonyl acetic acid (10 mmol), 4-fluorobenzaldehyde (10 mmol), glacial acetic acid (15 ml) and piperidine (0.5 ml) at room temperature (22° C.) over a magnetic stirrer for 5 hours. The mixture was then diluted with ether and the ethereal layer was washed with water. Evaporation of the ethereal layer yielded a semisolid material which on treating with 2-propanol gave a white solid. Recrystallization with 2-propanol gave 2-(4-chlorobenzyl sulfonyl)-3-(4-fluorophenyl)propenoic acid as white crystals, (yield 32%), m.p. 111–112° C. The above carboxylic acid derivative (10 mM) was made into an active ester by treatment with 10 mM 1-ethyl-3-(3-dimethylaminopropyl)carbodiimide hydrochloride (EDC) and 10 mM N-hydroxysuccinamide (NHS), and then cross-linked to KLH by mixing with 1 ml of a KLH water solution containing 500 mg KLH. The mixture was stirred at room temperature for 5–6 hours. The KLH conjugate was then separated by passing the mixture through a size exclusion column (PD 10, Pharmacia). The conjugate was then used to inject rabbits for raising antibodies.

All references cited with respect to synthetic, preparative and analytical procedures are incorporated herein by reference.

The present invention may be embodied in other specific forms without departing from the spirit or essential attributes thereof and, accordingly, reference should be made to the appended claims, rather than to the foregoing specification, as indication the scope of the invention.

What is claimed is:

1. A pharmaceutical composition comprising a pharmaceutically acceptable carrier and a compound of the formula:

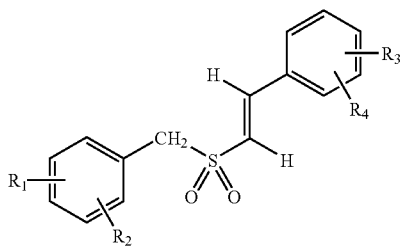

wherein:
$R_1$, $R_2$, $R_3$, and $R_4$ are independently selected from the group consisting of hydrogen, fluoro, chloro, bromo, C1–C6 alkyl, C1–C6 alkoxy, nitro, cyano and trifluoromethyl, with the proviso that:
(a) $R_1$, $R_2$, and $R_3$ may not all be hydrogen when $R_4$ is 2-chloro or 4-chloro;
(b) when $R_1$ and $R_3$ are hydrogen and $R_2$ is 4-bromo or 4-chloro, then $R_4$ may not be 4-chloro, 4-fluoro or 4-bromo;
(c) when $R_1$ and $R_3$ are hydrogen and $R_2$ is 4-fluoro, then $R_4$ may not be 4-fluoro or 4-bromo;
(d) when $R_1$ is hydrogen, and $R_4$ is 2-fluoro, then $R_2$ and $R_3$ may not be 4-fluoro; and
(e) when $R_1$ is hydrogen and $R_3$ is 4-hydrogen, 4-chloro, 4-bromo, 4-methyl or 4-methoxy, and $R_4$ is 2-hydrogen, 2-chloro, or 2-fluoro, then $R_2$ may not be 4-hydrogen, 4-chloro, 4-fluoro, or 4-bromo.

2. The composition according to claim 1 wherein the compound is selected from the group consisting of (E)-4-fluorostyryl-4-trifluoromethyl-benzylsulfone, (E)-2-trifluoromethyl-4-fluorostyryl-2,4-dichlorobenzyl-sulfone and (E)-4-fluorostyryl-4-cyanobenzylsulfone, (E)-4-fluorostyryl-3,4-dichlorobenzylsulfone, (E)-4-fluorostyryl-2,4-dichlorobenzylsulfone, (E)-2-chloro-4-fluorostyryl-4-chlorobenzylsulfone, and (E)-4-fluorostyryl-4-nitrobenzylsulfone, (E)-4-chlorostyryl-4-nitrobenzylsulfone, (E)-4-nitrostyryl-4-fluorobenzylsulfone, (E)-4-nitrostyryl-4-bromobenzylsulfone, (E)-4-nitrostyryl-4-cyanobenzylsulfone, (E)-4-fluorostyryl-4-methoxy-benzylsulfone, (E)-4-chlorostyryl-4-methoxybenzylsulfone, (E)-4-bromostyryl-4-methoxybenzylsulfone and (E)-4-nitrostyryl-4-methoxybenzylsulfone.

3. A method of treating an individual for cancer comprising administering an effective amount of a pharmaceutical composition according to claim 1.

4. A method of treating an individual for cancer comprising administering an effective amount of a pharmaceutical composition according to claim 2.

5. The method of according to claim 3 wherein the cancer is selected from the group consisting of ovarian, breast, prostate, lung, renal, colorectal and brain cancers.

6. The method of according to claim 4 wherein the cancer is selected from the group consisting of ovarian, breast, prostate, lung, renal, colorectal and brain cancers.

7. A method of inducing apoptosis of tumor cells in an individual afflicted with cancer comprising administering to said individual an effective amount of a pharmaceutical composition according to claim 1.

8. The method according to claim 7 wherein the tumor cells are selected from the group consisting of ovarian, breast, prostate, lung, colorectal, renal and brain tumors.

* * * * *